(12) United States Patent
Nitta et al.

(10) Patent No.: US 6,511,949 B1
(45) Date of Patent: Jan. 28, 2003

(54) OPHTHALMIC COMPOSITION WITH REGULATED VISCOSITY

(75) Inventors: Hiroo Nitta, Hyogo; Kaori Ogawa, Osaka, both of (JP)

(73) Assignee: Rohto Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 09/127,629

(22) Filed: Aug. 3, 1998

Related U.S. Application Data

(63) Continuation-in-part of application No. PCT/JP97/00267, filed on Feb. 4, 1997.

(30) Foreign Application Priority Data

Feb. 7, 1996 (JP) .............................................. 8-021256

(51) Int. Cl.⁷ .............................................. C11D 43/00
(52) U.S. Cl. ...................... 510/112; 510/115; 510/421; 510/473; 510/500; 424/78.04; 424/78.23; 424/78.36
(58) Field of Search ................................ 510/112, 115, 510/421, 473, 500; 424/78.04, 78.23, 78.36

(56) References Cited

U.S. PATENT DOCUMENTS

| | | | | |
|---|---|---|---|---|
| 3,882,036 A | * | 5/1975 | Krezanoski et al. | 510/112 |
| 3,884,826 A | * | 5/1975 | Phares, Jr. et al. | 252/106 |
| 3,920,810 A | * | 11/1975 | Rankin | 424/78.04 |
| 3,954,644 A | * | 5/1976 | Krezanoski et al. | 510/112 |
| 4,120,949 A | * | 10/1978 | Bapatla et al. | 424/78.04 |
| 4,409,205 A | | 10/1983 | Shively | 424/78 |
| 4,440,662 A | * | 4/1984 | Tsuzuki et al. | 510/112 |
| 4,783,488 A | | 11/1988 | Ogunbiyi et al. | 514/635 |
| 5,209,865 A | * | 5/1993 | Winterton et al. | 134/22.19 |
| 5,298,182 A | * | 3/1994 | Tsao et al. | 510/112 |
| 5,368,868 A | * | 11/1994 | Winicov | 424/667 |
| 5,411,598 A | * | 5/1995 | Tsao et al. | 134/26 |
| 5,451,398 A | | 9/1995 | Vigh | 424/78.04 |
| 5,532,224 A | | 7/1996 | Desai et al. | 514/63 |
| 5,591,426 A | * | 1/1997 | Dabrowski et al. | 424/78.04 |
| 5,604,189 A | * | 2/1997 | Zhang et al. | 510/112 |
| 5,616,348 A | * | 4/1997 | Winicov | 424/667 |
| 5,648,074 A | | 7/1997 | Park et al. | 424/94.2 |
| 5,654,262 A | | 8/1997 | Desai et al. | 510/115 |
| 5,773,396 A | * | 6/1998 | Zhang et al. | 510/115 |

FOREIGN PATENT DOCUMENTS

| | | | |
|---|---|---|---|
| CA | 2125060 | | 1/1995 |
| WO | 9500620 | | 1/1995 |
| WO | 9517492 | | 6/1995 |
| WO | 97/28827 | * | 8/1998 |

OTHER PUBLICATIONS

Siebenbrodt, I. et al., "Poloxamer–Systeme als potentielle Ophthalmika Teil 1: Viskose Polymerten–sidlösungen", PZ–Wissenschaft, DE., Verlag, Eschborn, vol. 3, No. 5, 1992 (pp. 135–141).

\* cited by examiner

*Primary Examiner*—William Krynski
*Assistant Examiner*—Dawn L. Garrett
(74) *Attorney, Agent, or Firm*—Rothwell, Figg, Ernst & Manbeck

(57) ABSTRACT

An ophthalmic composition having regulated viscosity characterized in that it contains polyoxyethylene polyoxypropylene glycol or polyoxyethylene-polyoxypropylene-substituted ethylenediamine in association with a pharmaceutically acceptable thickener and has a viscosity ranging from 1 cps to 8 cps at 200° C., which is useful as contact lens wetting solution, eye drops, cleaning agent, and preservative for contact lenses.

23 Claims, 2 Drawing Sheets

US 6,511,949 B1

OPHTHALMIC COMPOSITION WITH REGULATED VISCOSITY

This application is a continuation-in-part of PCT international application No. PCT/JP97/00267 which has an international filing date of Feb. 4, 1997 which designated the United States, the entire contents of which are hereby incorporated by reference.

TECHNICAL FIELD

The present invention relates to an ophthalmic composition and, more particularly, it relates to a composition containing polyoxyethylene polyoxypropylene glycol or ethylenediamine substituted with polyoxyethylene polyoxypropylene in association with a thickener, whereby the viscosity thereof is regulated or adjusted to a certain range. The composition of the present invention is useful as an ophthalmic solution, especially, as a solution which is usable as eye drops applicable to eyes while wearing contact lenses, as well as a contact lens wetting agent (solution), in order to reduce troubles caused by dry-eye (xerophthalmus) and the use of contact lenses.

BACKGROUND ART

Hard contact lenses have first been developed, but they had disadvantages such as inferior properties in wearing feeling and oxygen permeability. Oxygen permeable hard contact lenses have then been developed, some of which can be extendedly used for about 1 week. However, they still have drawbacks in wearing feelings and the like. Soft contact lenses have also been developed to improve wearing feelings. Lenses of this type are flexible and show improved fitting feelings and are used widely. However, the existing contact lenses, irrespective of the type, cannot be free from problems caused by inserting foreign materials into eyes. Troubles of various types could arise upon fitting and while wearing.

When fitting contact lenses to eyes, it is desirable that the lenses are made of hydrophilic materials with a surface of a nature being apt to get wet so that the lenses can be fitted accurately and safely on the cornea which is always dampened with lacrimal fluid. However, hard contact lenses and oxygen permeable hard contact lenses hardly get wet, because they are prepared using hydrophobic polymethyl methacrylate and polysiloxanyl methacrylate, respectively, as the basic material. Contact lens wetting solutions, which can form a hydrophilic layer on the surface of the contact lenses thereby improving the wettability of lenses made of hydrophobic material, have been provided. However, such existing wetting solutions contain plentiful thickening agents so as to facilitate the fitting, and the viscosity thereof usually reaches as high as 50 cps [centipoise; $10^{-3}$ Pa·s (Pa·s=kgm$^{-1}$s$^{-1}$)] or higher. Therefore, such solutions often arise unpleasant sticky feeling and troubles due to the existence of a highly viscous solution between the cornea and a contact lens. For example, a lacrimal fluid exchange between the cornea and a contact lens is damaged, which in turn might cause oxygen deficiency and induce ocular disorders such as corneal edema, corneal epithelial erosion, corneal endodermis cytotoxicity, and the like. Further, it may bring about distortion, fuzz, etc. of images.

On the other hand, wetting solutions were not required in the case of soft contact lenses because they are made of hydrophilic materials with high water content. Contact lenses easily adsorb proteins and lipids in lacrimal fluid in general and this tendency is remarkable in the case of soft contact lenses. It has become clear that, when such substances are attached and accumulated on the lens, wettability of the lens surface gets worse. Accordingly, even in the case of soft contact lenses, the development of useful and safe wetting solution is necessary.

With a progress in the materials for contact lenses, extendedly use of the lenses became possible and, as a result of a long-term wearing, problems such as unpleasant feeling while wearing and disorders of ocular tissues and also lenses are increasing. Such problems are mostly caused by the duration of a condition where lens surface cannot be sufficiently moistened by lacrimal fluid. Contact lenses have a property that their surface becomes dry soon after contacting to air. Thickness of the lens is about 100 μm in standard cases while the thickness of aqueous layer of lacrimal fluid is usually as thin as about 7 μm. Therefore, it is not quite easy to keep contact lenses wet with lacrimal fluid. In addition, a contact lens is apt to adsorb waste products such as hydrophobic proteins and lipids contained in tear, which, when accumulated, repel water extremely and make it more difficult for lacrimal fluid to stably cover the surface of the lens which is in a thin layer of tear.

When one uses contact lenses whose surface is hardly get wet due to some reasons, tear film hardly spread over the lens surface. As a result, the lens surface becomes dry, which may cause the damage of conjunctiva and cornea by a mechanical friction or the like. In addition, it is possible that the transparency of the lens is lowered, and that the refraction-correcting property thereof is deteriorated. Further, contaminants in or from outside of tear are apt to be adhered on the contact lenses, resulting in unpleasant feeling caused by foreign materials, clouding of contact lenses and the decrease in wetting ability. When such a condition is noted during the use of hard contact lenses, it has been treated with eye drops of artificial lacrimal fluid. However, because of the strong hydrophobicity of the contact lenses themselves, the wetting effect is not satisfactory. In the case of soft contact lenses, the lenses themselves are hydrophilic and, therefore, eye drops for improving the wettability of the lens surface while wearing have not been provided yet.

However, as previously mentioned, soft contact lenses are actually apt to adsorb contaminants in and from outside of tear to a great extent, and the wetting effect is extremely reduced due to the accumulation of such contaminants. Therefore, a suitable eye drops for soft contact lenses are also needed like in the case of contact lenses of other types. Further, recently, there is a tendency that xerophthalmus (dry-eye), a symptom where eyes become dry, is increasing and, accordingly, unpleasant feeling and diseases caused by dry-eye are now becoming a problem. Consequently, eye drops capable of improving the wettability of eye surface and being applied to eyes with or without contact lenses would be greatly useful and convenient.

As mentioned above, any types of contact lenses have a problem that the wettability of lens surface is deteriorated due to the property of the material and also the accumulation of adhered substances, which possibly results in disorders of ophthalmic tissues upon fitting and while wearing, and decreases the function of lenses themselves. In order to solve such a problem, it is desirable to use a wetting solution and/or eye drops capable of damping contact lenses sufficiently regardless of the material thereof, and are safe to human body. Usually, such a composition contains various components such as a thickener having a moisture-keeping effect, a surfactant having adsorption-preventing and solubility-promoting effects, a preservative, and the like. However, such components are easily adsorbed by contact lenses and accumulate on contact lenses. This tendency is significant particularly in the case of soft contact lenses. Therefore, in preparing eye drops, it is necessary to increase the amount of the surfactant for preventing the lenses from adsorbing the components. However, this is not preferable in terms of the influences to lenses and the safety to eyes. Accordingly, there has been a strong demand for the development of a composition usable as a contact lens wetting solution and/or eye drops, which is highly safe and free from the problem of accumulation and shows a durable wetting effect on both of eye tissue and contact lenses of hard- and soft-types.

Examples of known ophthalmologically safe surfactant free from adverse effect such as accumulation include polyoxyethylene polyoxypropylene glycol and polyoxyethylene polyoxypropylene substituted ethylenediamine. There have been disclosed a cleaning agent for contact lenses utilizing their cleaning and moistening (moisturizing) ability (Japanese Patent Publication (KOKAI) 87,346/1974 corresponding to U.S. Pat. Nos. 3,882,036 and 3,954,644), Japanese Patent Publication (KOKAI) 313,721/1992 corresponding to U.S. Pat. No. 5,209,865and European Patent Publication 439,429) and Japanese Patent Publication (KOKOKU) 63,885/1988 (corresponding to U.S. Pat. No. 4,440,662). A cleaning agent containing polyoxyethylene polyoxypropylene glycol and a thickener, which can be used to clean contact lenses while being attached onto eyes has been disclosed (Japanese Patent Publication (KOKOKU) 28922/1978). However, all of the cleaning agents disclosed in the literatures above are intended to remove the contaminants adhered onto the surface of the contact lenses. These literatures do not disclose or suggest any compositions which show wetting effect upon fitting and while wearing continuously. As mentioned already, contact lens wetting agent and eye drops containing a thickener in association with a surfactant have been known, but the existing products have disadvantages due to extra high viscosity. Further, a thickener shows excellent moisturizing effect due to its residing ability, which, however, does not necessarily mean that the moisturizing effect continues for a sufficient period of time or the lenses get wet quickly. Accordingly, for preparing a composition which is useful as a contact lens wetting agent and/or eye drops, it is necessary to compound appropriate surfactant and thickener in an appropriate ratio. However, there have been no such information in the prior arts.

DISCLOSURE OF INVENTION

The present inventors have studied intensively with an object of providing an ophthalmic composition containing highly safe components, which are useful to improve the unpleasant feeling due to xerophthalmus and has suitable moistening (moisturizing) effect on contact lenses of any type even during use, said moisturizing effect being durable for a sufficient period. The inventors have found that an intended composition can be obtained by compounding appropriately polyoxyethylene polyoxypropylene glycol or polyoxyethylene polyoxypropylene substituted ethylenediamine, which has proved to have no adverse effect on contact lenses such as accumulation and be safe, in association with a pharmaceutically acceptable thickener.

Thus, the present invention provides an ophthalmic composition having regulated viscosity characterized in that it contains polyoxyethylene polyoxypropylene glycol or polyoxyethylene-polyoxypropylene-substituted ethylenediamine in association with a pharmaceutically acceptable thickener and has a viscosity ranging from 1 cps to 8 cps at 20° C.

Throughout the present specification, the term "viscosity" used in connection with an ophthalmic composition of the present invention principally stands for a value measured at 20° by a method using a rotary viscometer of a cone-plate type which will be mentioned later.

The composition of the present invention has various uses in the field of ophthalmology. For example, since the moisture-keeping effect of a thickener due to the residing property as well as the moistening (moisturizing) effect of polyoxyethylene polyoxypropylene glycol or polyoxyethylene-polyoxypropylene-substituted ethylenediamine are potentiated, the composition has an excellent ability to make a solid surface to be liable to get wet, and is useful as a contact lens wetting agent. Further, since its moistening effect is durable, the composition is useful as eye drops applicable while wearing contact lenses. Furthermore, since the composition of the present invention comprises components free from adsorption with and accumulation on contact lenses, it is useful as a contact lens wetting agent and eye drops which have not been available prior to the present application. Still further, the composition of the present invention can moisten solid surface and therefore is expected to accelerate the wetting of cornea surface, whereby it is useful as eye drops for treating dry eye of patients with or without contact lenses. Besides, the composition is useful as a cleaning agent, preserving liquid, etc. for contact lenses.

BEST MODE FOR CARRYING OUT THE INVENTION

Figure 1:
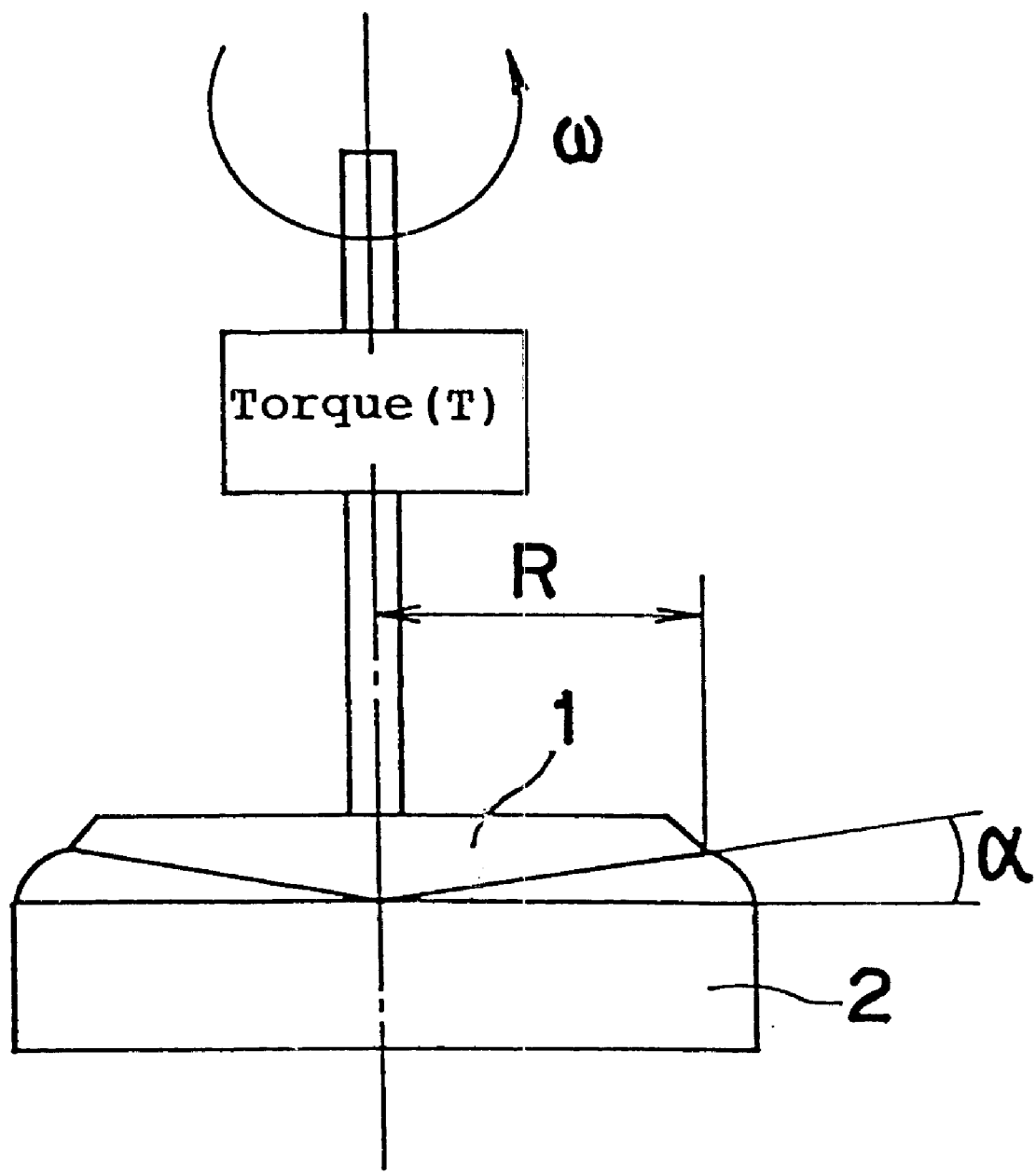
FIG. 1 is a rough sketch illustrating an example of a rotary viscometer of cone-plate type for measuring the viscosity.

Polyoxyethylene polyoxypropylene glycol used in the ophthalmic composition of the present invention is prepared by an addition polymerization of polypropylene glycol, which is prepared by an addition polymerization of propylene oxide, with ethylene oxide and is represented by the following formula.

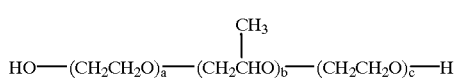

A compounds of the formula above is hereinafter referred to as "poloxamer". There are various poloxamers depending upon the average polymerization degrees of propylene oxide and ethylene oxide. Among them, poloxamer 124 (Pluronic L-44; aver. M.W. 2,200), poloxamer 188 (Pluronic F-68; aver. M. W. 8,350), poloxamer 235 (Pluronic P-85; aver. M. W. 4,600) and poloxamer 407 (Pluronic F-127; aver. M. W. 11,500) are preferred and poloxamers 188, 235 and 407 are particularly preferred.

Polyoxyethylene-polyoxypropylene-substituted ethylenediamine of poloxamine type can be shown by the following formula:

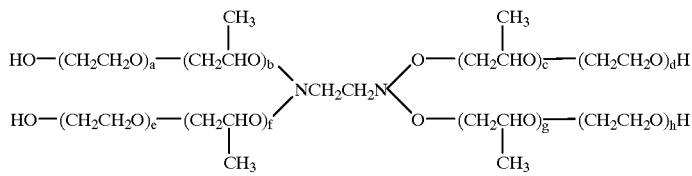

The compounds of the formula above is hereinafter referred to as "poloxamines". There are various poloxamines depending upon the average polymerization degrees of propylene oxide and ethylene oxide. Among them, Tetronic 707 (aver. M. W. 12,000), Tetronic 908 (aver. M. W. 22,500), Tetronic 1107 (aver. M. W. : 14,500), Tetronic 1307 (aver. M. W. 18,600) and Tetronic 1508 (aver. M. W. 26,600) are preferred and Tetronic 1107 is particularly preferred.

Any necessary poloxamers and poloxamines are commercially available from BASF Wyandotte Corporation or the like.

Examples of thickener useable in the ophthalmic composition of the present invention include gum arabic powder, sodium alginate, propylene glycol alginate, sodium chondroitin sulfate, sorbitol, dextran 70, tragacanth powder, sodium carboxymethyl cellulose, hydroxyethyl cellulose, hydroxypropylmethyl cellulose, carboxyvinyl polymer, triisopropanolamine, polyvinyl alcohol, polyvinylpyrrolidone and Macrogol 4000.

Among them, hydroxyethyl cellulose, hydroxypropylmethyl cellulose, polyvinyl alcohol and polyvinylpyrrolidone are preferred because they give a solution of an appropriate viscosity even at low concentrations. Hydroxyethyl cellulose and polyvinylpyrrolidone are more preferred since they are highly safe and do not affect contact lenses, although the present invention is not limited thereto.

The composition of the present invention contains a thickener(s) and one or more surfactants selected from the above-mentioned poloxamers and poloxamines in association with other pharmaceutically acceptable additives provided that the viscosity of the composition is within a range of 1 to 8 cps. The composition can be manufactured in accordance with a conventional method used for the preparation of eye drops.

In general, when the viscosity of a composition is too high, the wetting effect would rather be decreased and, when it is too low, a sufficient moisture-keeping effect cannot be expected. The present invention is based on the finding that, when a compound selected from poloxamers and poloxamines is present together with a thickening agent, effects thereof are potentiated even if the concentration of a thickener is lowered to adjust the viscosity of a composition considerably low as compared with conventional ones. Accordingly, the composition of the present invention solved the problems related to high-viscous compositions such as unpleasant sticky feeling, clouding of lenses, distortion of image, and the like, while maintaining a sufficient moistening effect. Further, because of the low viscosity, the lacrimal fluid exchange between the cornea and a contact lens is hardly inhibited and, therefore, the occurrence of ocular disorders due to oxygen deficiency including corneal edema, corneal epithelial erosion, corneal endodermis cytotoxicity, and the like can be prevented. These disorders are particularly serious in the case of soft contact lens which has a big diameter and thereby covering the whole area of cornea and is apt to closely adhere to cornea due to the softness. In addition, soft contact lenses are hardly get wet at viscosity of 8 cps or more and it becomes quite difficult to handle the lenses. According to the composition of the present invention, such a problem can be solved too.

It is more preferred that the viscosity of the present composition is 1 to 3 cps. When the viscosity is 3 cps or less, moistening effect of the composition increases and the feeling while wearing lenses is improved to an extent similar to that attainable by conventional eye drops. The viscosity of the present composition cannot be less than 1 cps when measured at 20° C., because the viscosity of distilled water used as a solvent for contact lens wetting agent and eye drops of the present invention is 1 cps at 20° C.

It is necessary to adjust the viscosity of the composition within the range as defined above for each case in accordance with a method known in the art, considering a combination of a poloxamer or poloxamine selected and a thickener, and also the kind of an additive(s).

The concentration of poloxamer or poloxamine in a composition of the present invention can be preferably between about 0.001–10%, more preferably 0.01–1%.

Various pharmaceutically acceptable substances which do not affect the contact lenses may be added to the ophthalmic composition of the present invention. For example, sodium chloride, potassium chloride, calcium chloride, sodium hydrogen phosphate, potassium phosphate, boric acid, borax, citric acid, sodium citrate, sodium carbonate, potassium aspartate, magnesium potassium aspartate, epsilon-aminocaproic acid, aminoethylsulfonic acid, sodium glutamate, hydrochloric acid, sodium hydroxide, acetic acid, glycerol, glucose, mannitol, etc. may be used as pH adjusting agents, buffers, isotonic agents, etc. It is also possible to use edetic acid and edetates (disodium edetate, calcium disodium edetate, trisodium edetate and tetrasodium edetate) as stabilizers; sorbic acid, potassium sorbate, ethyl p-oxybenzoate, butyl p-oxybenzoate, propyl p-oxybenzoate, methyl p-oxybenzoate, chlorhexidine gluconate, benzalkonium chloride, benzethonium chloride, alkyl polyaminoethylglycine and chlorobutanol as preservatives; and polysorbate 80, polyoxyethylene hydrogenated castor oil 60, urea, propylene glycol, Macrogol 4000, monoethanolamine and polyoxyethyleneoxystearic acid triglyceride as solubilizing adjuvants.

The usual single dosage of the present composition as eye drops is 1 to 3 drops and administered 3 to 6 times a day, preferably, 1 to 2 drops and administered 5 to 6 times a day. When it is used as a contact lens-wetting agent, 1 to 2 drops are applied onto a lens.

The present invention is further described in the following Examples, but should not be construed to limiting the scope of the present invention.

Viscosity of the ophthalmic composition of the present invention is measured by the following method or other ones yielding the equivalent results.

Method for Viscosity Measurement

Viscosity is measured by a method using a rotary viscometer of circular cone-plate type. This method is same as that mentioned in "*New Food Industry*, Vol. 22, No. 4–6, 1980 (by Taneichi Kawasaki)" and in "*The Japanese Pharmacopoeia*", 13th Revised Version, General Test Method, 36. Method of Viscosity Measurement, No. 2 Method Using a Rotary Viscometer, (3) Rotary Viscometer of a Cone-Plate Type.

(I) Measurement of Viscosity with a Rotary Viscometer of Cone-Plate Type

General method will be explained by referring to a simplified rotary viscometer of cone-plate type as shown in FIG. 1. First, a sample is placed in a gap between cone (1) and plate (2) having an angle of $\alpha$, then the cone (1) or the plate (2) is rotated with a certain angular velocity ($\omega$) or torque (T) to a stationary state, when the torque or angular velocity received by the plate (2) or the cone (1) is measured. The viscosity ($\eta$) of the sample is calculated as follows:

$$\eta=100\times(3\alpha/2\pi R^3)\cdot(T/\omega)$$

wherein:

$\eta$: viscosity of the sample (mPa·s) (Pa·s=$10^3$ cps)

$\alpha$: angle between the plate and the cone (rad)

$\pi$: pi

R: radius of the cone (cm)

T: torque acting on the plate or the cone surface ($10^{-7}$ N·m)

$\omega$: angular velocity (rad/s)

(II) Measurement of Viscosity of Ophthalmic Composition

Viscosity of the composition of the present invention can be measured by a commercially available rotary viscometer of cone-plate type and an appropriate rotor. Examples of such viscometer include viscometer of type E [manufactured by Tokimec and supplied by Toki Sangyo (Japan)], Synchro-Lectric of type PC (Brookfield, USA), Feranti Shirley (Feranti, England), Rotovisco™ (Hake, Germany), IGK Highsher rheometer (Ishida Giken, Japan), Shimadzu Rheometer™ (Shimadzu Seisakusho, Japan), Weissenberg Rheogoniometer (Sangamo, England), Mechanical Spectrometer (Rheometrics, U.S.A.), etc.

In the following Examples, the viscosity of a composition of the present invention was measured using a viscometer of E type (DVM-E viscometer) according to the teaching by the manufacturer. Therefore, a measuring method using the said apparatus will be explained in more detail below.

Figure 2:
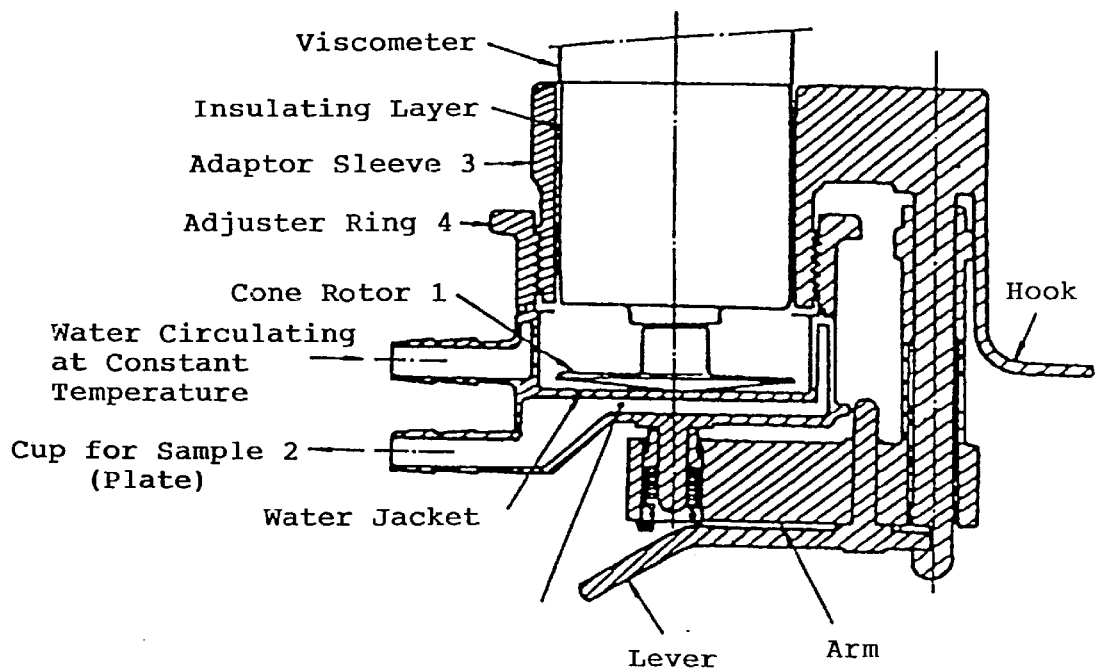
FIG. 2 is a longitudinally cross-sectioned side view of one rotary viscometer of a cone-plate type.
Figure 3:
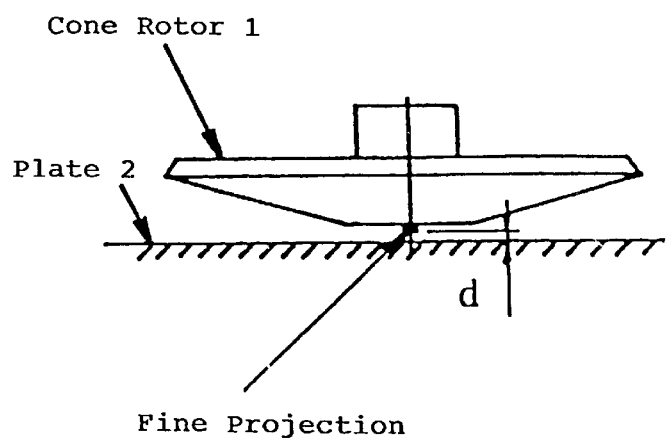
FIG. 3 is a front view showing the main part of the viscometer of FIG. 2.

The structure of DVM-E viscometer is shown in FIG. 2, wherein a cone rotor (1) (corresponding to the cone (1) mentioned in (I) above) shown in FIG. 3 is attached to the viscometer main body while a plate or a sample cup (2) (corresponding to the plate (2) mentioned in (I) above) to the adaptor sleeve (3). An adjuster ring (4) is in gear with an adaptor sleeve (3) by means of a screw and is constructed in such a manner that a cone rotor (1) and a plate (2) become closer or apart in accordance with the rotation thereof. As shown in FIG. 3, there is a fine projection at the center of the cone rotor (1) and the distance between the said projection and an imaginary vertex of the cone is defined as "d". The cone rotor (1) is rotated by a synchronous motor which rotates at a constant speed by means of a spring (both not shown). Under the condition, when a viscosity resistance torque of a liquid sample is applied to the rotor (1), the spring is distorted to the point where a good balance with said torque is achieved. Viscosity of the liquid is automatically calculated on the basis of the torsional angle and displayed on the instrument.

Conditions for Measurement

Upon measurement, a standard cone rotor (cone angle: 1° 34'; cone radius: 2.4 cm) attached to a DVM-E viscometer was rotated by a motor by means of a spring with a full-scale torque of 67.4 ×$10^{-6}$ Nm. The distance (d) from an imaginary vertex of the cone to the fine projection is 12.7 $\mu$m.

The viscometer is placed in such a manner that an axis of rotation was vertical to a horizontal plane. To the sample cup (2) was added 1 ml of a sample to be measured and the cup (2) was attached to the viscometer main body equipped with a cone rotor (1). The apparatus was allowed to stand until the temperature reaches 20° C. Then the apparatus was rotated at 50 rpm and the viscosity value displayed thereon was read. In order to obtain more accurate data, a hydrocarbon oil (Newton's fluid) of petroleum type defined as a standard liquid under JIS Z 8809 was used for calibration before measurement of the sample so as to adjust the measured value in agreement with the viscosity of the standard liquid. Viscosities of said standard liquid at 20° C., 30° C. and 40° C. are guaranteed with a precision of ±0.1%.

It would be easily understood by ordinary skilled in the art that the equivalent results could be obtained by the use of any commercially available apparatus other than the DVM-E type viscometer by selecting a cone rotor, measuring in the same manner as above, and calibrating appropriately.

EXAMPLE 1

Eye Drops

In 100 ml:

| | |
|---|---|
| Poloxamer 407 | 0.1 g |
| Hydroxyethyl cellulose | 0.1 g |
| Boric acid | 0.73 g |
| Borax | 0.05 g |
| Sodium chloride | 0.5 g |
| Potassium sorbate | 0.2 g |
| Sterilized water | q.s. |
| Total volume | 100 ml |

The above ingredients are aseptically compounded and filled to give eye drops (pH, about 7.2; osmotic ratio, about 1.1; and viscosity, 3 cps).

EXAMPLE 2

Contact Lens Wetting Solution

In 100 ml:

| | |
|---|---|
| Poloxamer 188 | 0.9 g |
| Hydroxyethyl cellulose | 0.2 g |
| Boric acid | 0.73 g |
| Borax | 0.05 g |
| Potassium chloride | 0.07 g |
| Sodium chloride | 0.43 g |
| Alkyl polyaminoethylglycine | 0.15 g |
| Sterilized water | q.s. |
| Total volume | 100 ml |

The above ingredients were aseptically compounded and filled to give a liquid for wetting the contact lenses (pH, about 7.2; osmotic ratio, about 1.0; viscosity, 5 cps).

EXAMPLE 3

Eye Drops

In 100 ml:

| | |
|---|---|
| Poloxamer 407 | 0.1 g |
| Polyvinyl alcohol | 0.2 g |
| Polyvinylpyrrolidone | 1.8 g |
| Potassium chloride | 0.1 g |
| Sodium chloride | 0.8 g |
| Potassium sorbate | 0.2 g |
| Sterilized water | q.s. |
| Total volume | 100 ml |

The above ingredients were aseptically compounded and filled to give an eye drops (pH, about 6.7; osmotic ratio, about 1.1; viscosity, 8cps).

EXAMPLE 4

Contact Lens Wetting Solution

In 100 ml

| | |
|---|---|
| Tetronic 1107 | 0.15 g |
| Methyl cellulose | 0.5 g |
| Hydroxypropylmethyl cellulose | 0.1 g |
| Boric acid | 0.73 g |
| Borax | 0.05 g |
| Sodium chloride | 0.5 g |
| Potassium sorbate | 0.2 g |
| Sterilized water | q.s. |
| Total volume | 100 ml |

The above ingredients were aseptically compounded and filled to give a liquid for wetting the contact lenses (pH, about 7.2; osmotic ratio, about 1.1; viscosity, 3 cps).

The moistening effect of the composition of the present invention on the surface of contact lenses was evaluated using the following experimental system. Thus, when one drop of eye drops is placed on a solid plane surface, the drop forms a hemispherical shape on the solid surface depending on a combination of the material of the solid, the droplet and the air layer. The angle between the tangential line on the liquid surface and the plane, which angle includes the droplet, is measured at the point where the surface of the droplet crosses the surface of the solid plane. It is noted that the less the said angle (herein referred to as θ), the more the affinity of the droplet to the solid surface, in other words, the liquid constituting the droplet (e.g., eye drops) is so-called wettable solution with regards the solid. In the following experimental examples, an experimental system established by improving the evaluation system above so as to comply with the object of the present invention is used. Specifically, the moistening effect is evaluated by placing a contact lens horizontally on a plane, pouring a droplet of eye drops over the front curve of the lens, which is opposite side to that contacts with cornea, and measuring the θ. Because the contact lens itself shares a partial shape of a sphere having a certain curvature, it is necessary to correct the angle ($θb$) between the tangential line on the liquid surface and the plane by subtracting the angle inherent to the lens ($θa$) previously measured from $θb$. That is, $θ=θb-θa$.

Measurement of θ can be easily conducted by, for example, a method where a picture is taken from the side face of the droplet placed over the contact lens or by a method where an image processing apparatus with a video camera is used. An oxygen-permeable hard contact lens was subjected to the measurement as it is, while a soft contact lens was subjected to the measurement after removing from a physiological saline to an air atmosphere to confirm that the surface is dry.

Experiment 1

Test solutions were prepared by dissolving polyoxyethylene polyoxypropylene glycol and hydroxyethyl cellulose or polyvinylpyrrolidone in distilled water at various concentrations and subjected to the measurement of the angle θ using an oxygen-permeable hard contact lens according to the above-mentioned evaluating method. Coefficient of oxygen permeation Dk value [$ml(O_2)cm/(cm^2 \cdot sec \cdot mmHg)$, 35° C.] of the lens was 60. Viscosity shows the absolute viscosity at 20° C. and is expressed by cps (centipoise) (1 cps=$10^{-3}$Pa·s; Pa·s=$kgm^{-1}s^{-1}$). viscosity was measured with a rotary viscometer. The results are shown in Table 1 below.

TABLE 1

θ(°) of Test Solutions to Oxygen-Permeable Hard Contact Lens

| Concentration (%) of POE POP Glycol | Concentration (%) of HEC or PVP | | Viscosity (cps) | θ (°) |
|---|---|---|---|---|
| 0 | | 0 | 1.00 | 85.3 |
| 0 | HEC | 0.10 | 2.60 | 35.8 |
| 0 | HEC | 0.30 | 7.80 | 37.4 |
| 0.10 | | 0 | 1.36 | 38.0 |
| 0.10 | HEC | 0.10 | 2.59 | 31.5 |
| 0.10 | HEC | 0.30 | 7.58 | 35.5 |
| 0.10 | HEC | 0.35 | 13.4 | 38.3 |
| 0.10 | HEC | 0.50 | 35.6 | 47.5 |
| 0.10 | PVP | 2.00 | 7.46 | 35.7 |

POE: polyoxyethylene
POP: polyoxypropylene
HEC: hydroxyethyl cellulose
PVP: polyvinylpyrrolidone

Experiment 2

Aqueous solutions each containing 0.1% poloxamer (poloxamer A, B or C), or a poloxamine with or without 0.1% hydroxyethyl cellulose were prepared and the angle θ was measured using the same oxygen-permeable hard contact lens used in the Experiment 1 according to the evaluating method above. The results are shown in Table 2 below.

TABLE 2

θ(°) of Test Solutions for Oxygen-Permeable Hard Contact Lens

| Poloxamer or Poloxamine (Concentration: 0.10%) | Concentration of HEC (%) | Viscosity (cps) | θ (°) |
|---|---|---|---|
| Poloxamine | 0 | 1.38 | 36.7 |
| | 0.10 | 2.67 | 29.2 |
| Poloxamer A | 0 | 1.42 | 43.5 |
| | 0.10 | 2.69 | 30.6 |
| Poloxamer B | 0 | 1.42 | 36.4 |
| | 0.10 | 2.56 | 29.6 |
| Poloxamer C | 0 | 1.41 | 30.9 |
| | 0.10 | 2.48 | 23.4 |

Experiment 3

Polyoxyethylene polyoxypropylene glycol and/or hydroxyethyl cellulose were/was dissolved in saline to prepare test solutions and, in accordance with the above-mentioned evaluating method, θ for soft contact lens of 37.5% water content was measured in a similar manner. The results are shown in Table 3 below.

TABLE 3

θ(°) of Test Solutions for Soft Contact Lens

| Concentration of POE-POP Glycol (%) | Concentration of HEC (%) | Viscosity (cps) | θ (°) |
|---|---|---|---|
| 0 | 0 | 1.0 | 71.9 |
| 0.10 | 0 | 1.36 | 41.6 |
| 0.10 | 0.10 | 2.59 | 23.0 |

It is clear from the tables that, the θ values for contact lens of any types are high when evaluated in distilled water or saline. However, the values significantly decreases when evaluated in solutions containing polyoxyethylene polyoxypropylene glycol, indicating that such solutions have an ability to allow the contact lens get wet. When the test solution contains a thickener in addition to polyoxyethylene polyoxypropylene glycol, further decrease in the θ values is observed. These facts indicate that the wetting ability of a solution increases as the viscosity decreases and that the extra high viscosity decreases the wetting ability.

Experiment 4

Duration of moistening effect of the composition of the present invention on the surface of a contact lens was evaluated using the following experimental system.

Solutions containing polyoxyethylene polyoxypropylene glycol and hydroxyethyl cellulose at various concentrations were prepared and used as test solutions. A test solution was placed in a beaker and a contact lens was completely dipped therein. Then, the contact lens was taken out from the solution and observed under a stereoscopic microscope of ten magnifications equipped with a coaxial downward lightening device as for the water wetting condition on the surface of the contact lens at its front curve side. The time (t) after taking out the lens from the test solution until the appearance of a dry part on the lens surface was measured and defined as the duration of wetting. The results are shown in Table 4 below.

TABLE 4

Time "t" (sec) of Each Test Solution for Oxygen-Permeable Hard Contact Lens

| Concentration of POE-POP Glycol (%) | Concentration of HEC (%) | Viscosity (cps) | t (sec) |
|---|---|---|---|
| 0 | 0.10 | 2.60 | 1.0 |
| 0 | 0.30 | 7.80 | 1.0 |
| 0 | 0.50 | 27.8 | 4.5 |
| 0.10 | 0 | 1.36 | 28.3 |
| 0.10 | 0.10 | 2.59 | 61.7 |
| 0.10 | 0.30 | 7.58 | 120.5 |
| 0.10 | 0.50 | 35.60 | 126.0 |

The above results show that, in the case of aqueous solutions containing hydroxyethyl cellulose alone, wetting on the surface of contact lens is not durable and dry parts soon appear even if the lens is once dipped in a solution to wet completely. However, in the case of aqueous solutions containing polyoxyethylene polyoxypropylene glycol alone, wetting on the surface of contact lenses is durable. Further, when the solution contains hydroxyethyl cellulose (a thickener) in addition to polyoxyethylene polyoxypropylene glycol, the duration of water wetting becomes longer compared to a solution containing polyoxyethylene polyoxypropylene glycol alone. However, even if the viscosity of the solution is further elevated, the duration of water wetting remains unchanged and, as shown in Experiment 1, the moistening effect is disadvantageously lowered.

The results of Experiments 1 to 4 show that the absolute viscosity of a composition of the present invention to be used mainly as a contact lens wetting solution and/or eye drops is preferably within a range of from 1 cps to 8 cps or, more preferably, from 1 cps to 3 cps at 20° C., in view of the elimination of sticky feeling, improvement of the lacrimal fluid exchange while wearing contact lenses, and the continuous moistening effect into consideration.

What is claimed is:

1. An ophthalmic composition comprising polyoxyethylene polyoxypropylene glycol at a concentration of between 0.001–10% in association with a pharmaceutically acceptable thickener and wherein said composition has a viscosity ranging from 1 cps to 8 cps at 20° C., wherein the thickener is selected from the group consisting of gum arabic powder, sodium alginate, propylene glycol alginate, sodium chondroitin sulfate, sorbitol, dextran, tragacanth powder, hydroxyethyl cellulose, hydroxypropylmethyl cellulose, carboxyvinyl polymer, triisopropanolamine, polyvinyl alcohol, polyvinylpyrrolidone and macrogol.

2. The ophthalmic composition of claim 1, wherein the viscosity is between 1 cps and 3 cps.

3. The ophthalmic composition of claim 1, wherein the thickener is selected from the group consisting of hydroxyethyl cellulose, hydroxypropylmethyl cellulose, polyvinyl alcohol and polyvinylpyrrolidone.

4. The ophthalmic composition of claim 1, wherein the composition is a contact lens wetting solution.

5. An ophthalmic composition for contact lens, comprising polyoxyethylene polyoxypropylene glycol at a concentration of between 0.001–10% in association with a pharmaceutically acceptable thickener and having a viscosity ranging from 1 cps to 8 cps at 20° C., wherein the thickener is selected from the group consisting of gum arabic powder, sodium alginate, propylene glycol alginate, sodium chondroitin sulfate, sorbitol, dextran, tragacanth powder, hydroxyethyl cellulose, hydroxypropylmethyl cellulose, carboxyvinyl polymer, triisopropanolamine, polyvinyl alcohol, polyvinylpyrrolidone and macrogol.

6. The ophthalmic composition of claim 5, wherein the viscosity is between 1 cps and 3 cps.

7. The ophthalmic composition of claim 5, wherein the thickener is selected from the group consisting of hydroxyethyl cellulose, hydroxypropylmethyl cellulose, polyvinyl alcohol and polyvinylpyrrolidone.

8. The ophthalmic composition of claim 5, wherein the composition is useful for cleaning or preserving a contact lens.

9. A method of treating the eye of a patient suffering from dry eye, comprising contacting said eye with an ophthalmic composition comprising polyoxyethylene polyoxypropylene glycol at a concentration of between 0.001–10% in association with a phamaceutically acceptable thickener and having a viscosity ranging from 1 cps to 8 cps at 20° C.

10. The method of claim 9, wherein the dry eye is related to wearing a contact lens.

11. Eye drops comprising polyoxyethylene polyoxypropylene glycol at a concentration of between 0.001–10% in association with a pharmaceutically acceptable thickener and having a viscosity ranging from 1 cps to 8 cps at 20° C.

12. The eye drops of claim 11, wherein the viscosity is between 1 cps and 3 cps.

13. The eye drops of claim 11, wherein the thickener is selected from the group consisting of gum arabic powder, sodium alginate, propylene glycol alginate, sodium chondroitin sulfate, sorbitol, dextran, tragacanth powder, hydroxyethyl cellulose, hydroxypropylmethyl cellulose, carboxyvinyl polymer, triisopropanolamine, polyvinyl alcohol, polyvinylpyrrolidone and macrogol.

14. The eye drops of claim 11, wherein the thickener is selected from the group consisting of hydroxyethyl cellulose, hydroxypropylmethyl cellulose, polyvinyl alcohol and polyvinylpyrrolidone.

15. The eye drops of claim 11, wherein said eye drops are usable while wearing contact lens.

16. A method for improving the moistening effect of an aqueous ophthalmic composition for contact lens on a surface comprising (a) adding to said composition polyoxyethylene polyoxypropylene glycol at a concentration of between 0.001–10% and a pharmaceutically acceptable thickener and (b) adjusting viscosity of the composition to between 1 cps to 8 cps at 20° C.

17. The method of claim 16, wherein the thickener is selected from the group consisting of gum arabic powder, sodium alginate, propylene glycol alginate, sodium chondroitin sulfate, sorbitol, dextran, tragacanth powder, sodium carboxymethyl cellulose, hydroxyethyl cellulose, hydroxypropylmethyl cellulose, carboxyvinyl polymer, triisopropanolamine, polyvinyl alcohol, polyvinylpyrrolidone and macrogol.

18. A method for improving the moistening effect of an aqueous ophthalmic composition for contact lens on a surface comprising (a) adding to said composition polyoxyethylene polyoxypropylene glycol at a concentration of between 0.001–10% and a pharmaceutically acceptable thickener and (b) adjusting viscosity of the composition to between 1 cps to 8 cps at 20° C.

19. The method of claim 18, wherein the thickener is selected from the group consisting of gum arabic powder, sodium alginate, propylene glycol alginate, sodium chondroitin sulfate, sorbitol, dextran, tragacanth powder, sodium carboxymethyl cellulose, hydroxyethyl cellulose, hydroxypropylmethyl cellulose, carboxyvinyl polymer, triisopropanolamine, polyvinyl alcohol, polyvinylpyrrolidone and macrogol.

20. A method for preparing an ophthalmic composition having potentiated and durable moistening effect on a surface comprising (a) adding to an aqueous composition polyoxyethylene polyoxypropylene glycol at a concentration of between 0.001–10% and a pharmaceutically acceptable thickener and (b) adjusting viscosity of the composition to between 1 cps to 8 cps at 20° C.

21. The method of claim 20, wherein the thickener is selected from the group consisting of gum arabic powder, sodium alginate, propylene glycol alginate, sodium chondroitin sulfate, sorbitol, dextran, tragacanth powder, sodium carboxymethyl cellulose, hydroxyethyl cellulose, hydroxypropylmethyl cellulose, carboxyvinyl polymer, triisopropanolamine, polyvinyl alcohol, polyvinylpyrrolidone and macrogol.

22. A method for preparing an ophthalmic composition for contact lens having potentiated and durable moistening effect on a surface comprising (a) adding to an aqueous composition polyoxyethylene polyoxypropylene glycol at a concentration of between 0.001–10% and a pharmaceutically acceptable thickener and (b) adjusting viscosity of the composition to between 1 cps to 8 cps at 20° C.

23. The method of claim 22, wherein the thickener is selected from the group consisting of gum arabic powder, sodium alginate, propylene glycol alginate, sodium chondroitin sulfate, sorbitol, dextran, tragacanth powder, sodium carboxymethyl cellulose, hydroxyethyl cellulose, hydroxypropylmethyl cellulose, carboxyvinyl polymer, triisopropanolamine, polyvinyl alcohol, polyvinylpyrrolidone and macrogol.

\* \* \* \* \*